United States Patent [19]

Schole et al.

[11] 3,988,434
[45] *Oct. 26, 1976

[54] DENTAL PREPARATION

[76] Inventors: Murray L. Schole, 487 Munroe Ave., North Tarrytown, N.Y. 10591; Richard S. Gubner, Middle Neck Road, Sands Point, Port Washington, N.Y. 11050

[ * ] Notice: The portion of the term of this patent subsequent to Oct. 17, 1989, has been disclaimed.

[22] Filed: Dec. 3, 1974

[21] Appl. No.: 529,189

Related U.S. Application Data

[60] Continuation of Ser. No. 278,247, Aug. 7, 1972, abandoned, which is a division of Ser. No. 434,678, Feb. 23, 1965, abandoned, which is a division of Ser. No. 778,329, Dec. 5, 1958, abandoned.

[52] U.S. Cl...................................... 424/54; 424/49
[51] Int. Cl.$^2$........................................... A61K 7/22
[58] Field of Search............................... 424/49, 54

[56] References Cited
UNITED STATES PATENTS

3,004,897  10/1961  Shore................................... 424/54

3,699,221  10/1972  Schole et al......................... 424/49

FOREIGN PATENTS OR APPLICATIONS

490,384  8/1938  United Kingdom................... 424/54

OTHER PUBLICATIONS

Pawlowska, J., "Strontium Chloride," Czaspismo Stomatologiczne, vol. 9, 1956, No. 7, pp. 353–361.

*Primary Examiner*—Lewis Gotts
*Assistant Examiner*—Cary Owens
*Attorney, Agent, or Firm*—Brooks Haidt Haffner & Delahunty

[57] ABSTRACT

A method for improving oral hygiene by applying to teeth a dentifrice containing strontium disodium ethylene diamine tetraacetate (EDTA) in effective amounts up to a strontium cation concentration of about 10%.

4 Claims, No Drawings

DENTAL PREPARATION

CROSS REFERENCES

This is a continuation of application Ser. No. 278,247, filed Aug. 7, 1972, which is a division of our copending application Ser. No. 434,678 filed Feb. 23, 1965, now abandoned, which is in turn a division of our application Ser. No. 778,329 filed Dec. 5, 1958, now abandoned.

BRIEF DESCRIPTION OF THE INVENTION

This invention is that of a method of promoting oral hygiene by topical application of a dentifrice containing strontium disodium tetraacetate.

More particularly, the products used in the method of this invention embrace any of the various types of dentifrice dosage forms and comprise as the essential constituent (i) a pharmacologically innocuous water-soluble strontium chelate of ethylene diamine tetraacetic acid (EDTA), or (ii) a water-soluble salt of EDTA together with a pharmacologically innocuous water-soluble strontium salt that can react in an aqueous medium with such EDTA salt to give the corresponding strontium chelate.

It has been found that the dentifrice preparations used in the method of this invention are beneficial and, merely by topical application, readily contribute effective improvement particularly in treatment of hypersensitive dentin, periodontitis and gingivitis and provide conditions conducive to the promotion of good dental hygiene and the possibility of prophylaxis in relation to various dental disorders. To illustrate, in many cases the keen sensitiveness to hot and to cold and the resulting, frequently intense, pain characteristic of hypersensitive dentin, was observed to disappear even after only a very short period of treatment. It has also been discovered that such treatments are effective in removing plaque and in preventing plaque build-up.

The method of the invention involves promoting oral hygiene, e.g. by alleviating hypersensitive dentin, by a procedure which comprises administering to the oral cavity a dentifrice of the type and constitution herein described, allowing the constituents of such dentifrice, that are effective for alleviating hypersensitive dentin, i.e. the strontium and chelate content, while in the aqueous medium in the mouth to contact at least the exposed sensitive areas of any of the teeth that manifest hypersensitive dentin, for a time sufficient for relief from such sensitivity to appear, and repeating such application of such strontium disodium EDTA chelate content when necessary and at intervals as necessity for such repetition occurs. Best results are obtained by having patients follow a fixed routine, e.g. by having them brush their teeth with the dentifrice for at least one minute twice a day. As beneficial results are established reduced frequency can be tolerated.

Thus, broadly the method of the invention comprises applying to the teeth a dentifrice composition that provides cationic strontium under aqueous conditions during its use in the oral cavity and, associated with such cationic-strontium-providing content in the composition, a chelate residue of a strontium disodium EDTA chelate.

The amount of strontium disodium EDTA present in the dentifrice must be sufficient to produce the desired therapeutic and hygienic results. Effective amounts include concentrations of strontium cation of the chelate compound in the range of about 2.5% up to about 10% by weight of said toothpaste, concentrations of 2.5 to 7.5% being preferred.

The dentifrice products used should not include any calcium or other metal, salt or compound, from which any such metal would be sequestered by, and form the corresponding calcium or other metal chelate with, the EDTA salt or the chelate residue of the strontium chelate in the product.

In other words, the dentifrice products of the invention should not include any of the water-insoluble calcium, magnesium, or aluminum compounds ordinarily incorporated as adjuvant bulk excipients generally used in dentifrices, for example as the abrasive ingredient, such as calcium carbonate, calcium pyrophosphate, magnesium oxide, aluminum oxide or hydroxide, and the like. So also tin compounds, e.g. stannous fluoride and stannous chlorofluoride, likewise should be excluded.

In place of the foregoing water-insoluble bulk excipients for abrasive and other purposes, water-insoluble barium and strontium salts, for example, barium sulphate, barium carbonate, strontium carbonate, and strontium phosphate can be used. The dentifrice should contain a surface-active wetting agent compatible with strontium ions in an aqueous solution. Suitable wetting agents are tetra-oxyethylene sorbitan mon-oleate and Tween 80.

Dental clinical investigators have wrestled long with such problems as alleviating or overcoming hypersensitive dentin, and with others of the quite common dental ailments. While various treatments have been tried for hypersensitive dentin and also for others of the ailments, and others were considered and studied, each approach still shows its own various peculiar shortcomings so that the problems involved have not yet been solved sufficiently satisfactorily.

A distinctive feature of the invention is that by mere topical application of a strontium disodium EDTA containing dentifrice there occurs at least in part the effecting or an exchange mineralization between the calcium of the insoluble hydroxyapatite of the tooth and the strontium of the strontium chelate, or strontium salt and chelating agent, of the new dentifrice, and with beneficial therapeutic results.

The chelating agent or residue in the dentifrice serves to enhance the indicated exchange mineralization. When the teeth are contacted by the strontium chelating of the dentifrice in the mouth fluids, calcium ions are removed from the hydroxyapatite of the teeth and are preferentially sequestered displacing strontium and yielding the calcium chelate instead while at the same time the thus released strontium ions in turn replace in the tooth hydroxyapatite the calcium ions that were removed.

The resulting strontium hydroxyapatite is less soluble than the original (i.e. calcium) hydroxyapatite, the natural principal constituent of the teeth. Such strontium hydroxyapatite is more resistant to the solubilizing effect of general or local lowered pH in the mouth, which latter condition is one generally recognized to be a factor in the dissolution of the tooth surface enamel, for example, as in dental caries.

Strontium hydroxyapatite is more resistant not only to dissolution by the acidic substances occurring in the oral cavity, such as lactic and citric acids and amino acids, but also to the chelating effect of these organic acids as well as that of others of the various organic substances that have chelating effects such as food residues and those formed by bacterial action. Such chelating action also is considered to play a part in the loss of calcium from enamel with dissolution or tooth substance.

The following examples of several different types of dentifrices illustrate the invention, although its scope as to type and composition is not restricted to them.

EXAMPLE 1 - TOOTH PASTE

| | |
|---|---|
| Disodium Salt of Ethylenediamine Tetraacetic Acid | 20 grams |
| Strontium Chloride ($6H_2O$) | 20 grams |
| Strontium Carbonate | 25 grams |
| Tetra-oxyethylene sorbitan mono-oleate | 0.5 gram |
| Algin | 1 gram |
| Essential Oils (for flavoring) | 1 gram |
| Propylene Glycol | 25 grams |
| Alcohol | 0.9 gram |
| Water quantity sufficient to make | 100 grams |

EXAMPLE 2 - TOOTH PASTE

| | |
|---|---|
| Disodium strontium ethylenediamine tetraacetate | 30 grams |
| Barium Sulfate | 30 grams |
| Tetra-oxyethylene sorbitan mono-oleate | 0.5 gram |
| Algin | 1 gram |
| Essential Oils (for flavoring) | 1 gram |
| Propylene Glycol | 20 grams |
| Alcohol | 0.9 gram |
| Water quantity sufficient to make | 100 grams |

The customary methods are applicable to preparing the foregoing toothpaste. For example, the finely divided solid ingredients can be mixed dry and then incorporated in the mixed liquid ingredients (as the propylene glycol, water and alcohol). Then the essential oils for flavoring can be worked in.

EXAMPLE 3 - TOOTH PASTE

| | |
|---|---|
| Disodium salt of EDTA | 6.6 grams |
| Strontium chloride ($6H_2O$) | 5.0 grams |
| Strontium carbonate | 25.0 grams |
| Methyl salicylate | 1.25 grams |
| Water | 33 cc |
| Natrosol | 1.7 grams |
| Tween 80 | 1.3 grams |
| Cpc | .3 gram |
| Sodium saccharin | 1.2 grams |
| Propylene glycol | 25 cc |

EXAMPLES 4–6 - TOOTH PASTE

| | Preparation | | | |
|---|---|---|---|---|
| | 4 | 5 | 6 | |
| Disodium salt of ethylene diamine tetraacetic acid | 22.5 | 18.0 | 11.25 | grams |
| Strontium chloride ($6H_2O$) | 17.5 | 12.8 | 8.5 | grams |
| Strontium carbonate | 25.0 | 25.0 | 25.0 | grams |
| Cetyl pyridinium chloride | 0.5 | 0.5 | 0.5 | gram |
| Oil of cassia | 0.75 | 0.75 | 0.75 | gram |
| Oil of wintergreen | 1.0 | 1.0 | 1.0 | grams |
| Propylene glycol | 25.0 | 25.0 | 25.0 | grams |
| Natrosol | 1.7 | 1.7 | 1.7 | grams |
| Saccharin | 1.2 | 1.2 | 1.2 | grams |
| Tween 80 | 1.3 | 1.3 | 1.3 | grams |
| Water QSAD to 100 grams | | | | |

The strontium EDTA dentifrice of Examples 3–6 was used by 54 randomly selected patients by brushing their teeth at home twice a day with the toothpaste for at least one week allowing at least one minute per brushing. Some of the patients were given the toothpaste to use as routine prophylaxis and some of the patients were given the toothpaste to alleviate conditions diagnosed as periodontitis, gingivitis and hypersensitive dentin. The results are shown in the attached Table I.

In general, the patients using the toothpaste as routine prophylaxis reported stain removal, that calculus or film did not collect on teeth and that teeth felt cleaner. These reports were confirmed by observation. The reports of a clean, smooth and silky feeling or a polished effect indicates the removal or prevention of accumulation of plaque or pellicle.

The patients having a hypersensitive dentin condition all reported alleviation of this condition.

In the patients having gingivitis, there was an observed improvement in all cases indicated by a reduction or stoppage of bleeding and a reduction of edema.

In the patients having periodontitis, there was an observed improvement in all cases indicated by a reduction or stoppage of bleeding, a reduction of edema, absence of plaque, and an improvement in gingival tone and color.

TABLE I

| Name | Age | Sex | Prep. Used | No. of weeks used | Diagnosis (or reasons for use) | Voluntary Comment | Observation |
|---|---|---|---|---|---|---|---|
| L.D. | 61 | F | 4 | 1 | Periodontitis (advanced) Hypersensitive dentin | Reported "soothing" effect on gums. Bleeding diminished. Sensitivity alleviated. | Edema and bleeding reduced Hypersensitivity alleviated. Plaque noticeably absent. |
| D.F. | 35 | F | 4 | 2 | Periodontitis | Clean fresh morning mouth. Teeth feel very clean. | Edema reduced. Tone and color improved. |
| A.D. | 34 | F | 4 | 2 | Periodontitis | Teeth feel very clean. Gums feel better. | Edema reduced. Bleeding diminished. Tone & color improved. |
| M.C. | 53 | F | 4 | 3 | Routine | Teeth feel extremely clean. Fresh taste. Food film does not cling to teeth. Gums look pinker. | Improvement in gingival tone and color. Teeth whiter. |
| P.C. | 21 | F | 4 | 1 | Routine | No feeling of film on teeth after eating or drinking. Terrific polish. | Teeth brighter and whiter. |
| H.L. | 47 | M | 4 | 1 | Hypersensitivity | Hypersensitivity completely relieved. Clean feeling. | Hypersensitivity completely relieved. Teeth whiter. |
| T.B. | 21 | M | 4 | 1 | Acute gingivitis | Bleeding stopped. | Edema and bleeding markedly diminished. |
| P.M. | 54 | F | 4 | 2 | Routine | Teeth very clean. Teeth look whiter. | Teeth appeared brighter. Stains removed. |

TABLE I-continued

| Name | Age | Sex | Prep. Used | No. of weeks used | Diagnosis (or reasons for use) | Voluntary Comment | Observation |
|---|---|---|---|---|---|---|---|
| R.F. | 32 | F | 4 | 2 | Periodontitis | Whitens teeth. Gets teeth really clean. Soothes gums. | Edema considerably less. Bleeding diminished. |
| J.F. | 35 | M | 4 | 1 | Routine | 3 or 5 brushings removed all stains - teeth very clean. | Persistent stains removed. |
| D.V.H. | 40 | F | 4 | 1 | Routine | Clean feeling after brushing quite superior to regular toothpaste. | Teeth brighter and stains removed. |
| B.W. | 60 | F | 4 | 1 | Routine, Mouth odor. | Nice clean feeling. Stains removed. | Mouth deodorized. Stains removed. |
| E.C. | 56 | F | 4 | 1 | Routine | Nice clean feeling. Stains removed. | Stains removed. |
| M.K. | 46 | F | 4 | 1 | Periodontitis Hypersensitivity | Gums felt better. Teeth were not sensitive. | Gingival tone & color improved (observed by patient's hygienist) |
| L.S. | 28 | F | 4 | 3 | Gingivitis, many stains heavy tobacco user. | Gleem and Macleans did not remove stains. Sr. Ch. produced stain, removal, deodorized mouth, reduced gum bleeding. | Marked improvement in gingival tone & color Bleeding diminished, stains noticeably absent. |
| P.S. | 48 | F | 4 | 3 | Periodontitis. Many stains on lower anteriors. | Persistent stains removed after one week of use - deodorized mouth - very clean feeling. | Stains removed. Improvement in gingival tone and color. |
| E.R. | 47 | M | 4 | 1 | Routine care. | Salty taste. Cleans teeth well. Clean feeling. | Noticeable stain and calculus removed. |
| R.R. | 27 | F | 4 | 3 | Chronic marginal periodontitis. Noticeable plaque. | Noticed diminished bleeding. Very clean feeling. | Visible plaque absent. Marked reduction in edema. No bleeding. Improvement in color and tone. Odor removed. |
| F.P. | 34 | M | 4 | 3 | Heavy tobacco stains. | Removed stains from teeth better than any other tooth paste. | Stains gone, teeth brighter & whiter. |
| E.P. | 26 | F | 6 | 1 appl. | Hypersensitive Dentin. | Diminishing hypersensitivity. | Alleviated sensitivity to air and explorer. |
| J.M. | 36 | M | 4 | 1 | Hypersensitive dentin, heavy stains, gingivitis. | Sensitivity in upper anterior teeth completely relieved, stains removed. | Complete relief of hypersensitive dentin. Stains removed. |
| C.M. | 60 | F | 4 | 1 | Ulcer under palatal bar. Stains. Periodontitis. | Ulcer healing. Soothing effect on gums. | Ulcer healing. Stains removed. Improved gingival tone. |
| D.H. | 42 | F | 4 | 1 | Routine Care. Stains. | Cleans teeth well. Removed stains. | Stains removed. |
| C.H. | 30 | F | 4 | 2 | Chronic periodontitis. Excessive calculus formation. | Bleeding diminished. Mouth felt very clean as after dental prophylaxis. Clean feeling persisted for a prolonged time. | Bleeding and inflammation reduced. Calculus formation retarded. |
| J.N. | 22 | F | 4 | 1 | Periodontitis. Plaque formation extensive. | No film accumulation after eating. Teeth really feel clean. | Bleeding diminished. Reduction in edema. Improvement in gingival tone and color. |
| H.B. | 61 | F | 4 | 1 | Routine | Teeth feel very smooth and remain so. | Teeth brighter. Stains removed. |
| J.A. | 23 | F | 4 | 1 | Periodontitis. Severe Bleeding. | Gum bleeding stopped. | Severe bleeding greatly diminished. Edema reduced |
| E.L. | 42 | F | 4 | 2 | Periodontitis | Clean feeling persisted till following morning. | Edema reduced. Bleeding diminished. |
| R.M. | 34 | M | 4 | 1 | Routine. Cigar smoker. | Clean silky feeling. | Teeth brighter. Stains removed. Deodorizing effect. |
| B.M. | 45 | F | 4 | 1 | Routine | Clean feeling. | Teeth brighter. |
| D.T.1 | 21 | F | 4 | 1 | Acute necrotizing gingivitis. Fetor oris. | Cleans teeth very well, smooth feeling. Pleasant morning taste. Gums feel healthier. | Bleeding stopped. Edema reduced. Pronounced deodorizing effect. |
| D.T.2 | 21 | F | 4 | 1 | Gingivitis. Supply exhausted, 3 weeks ago. Fetor oris. | Great improvement noted again as previous. | Bleeding stopped. Edema reduced. Pronounced deodorizing effect. |
| P.T. | 69 | M | 4 | 3 | Peridontitis | Noticed calculus did not return. | After periodontal scaling calculus did not return during period of observation as it had done before without Sr.Ch. |
| P.Z. | 56 | F | 4 | 1 | Periodontitis | Unusual clean feeling. | Bleeding diminished. |
| C.B. | 45 | F | 4 | 1 | Routine | Tartar or film did not collect on teeth. Stayed cleaner longer. Removed mouth odor. | Teeth brighter. Stain removed. |
| M.H. | 28 | F | 4 | 1 | Routine | Cleans teeth very well. Mouth stays fresh longer. | Teeth whiter. |
| L.P. | 20 | F | 4 | 1 | Routine | Clean teeth and makes them feel silky. | Teeth appear brighter. |
| B.B. | 20 | M | 4 | 1 | Gingivitis. Acute necrotizing. Fetor oris. | Bleeding stopped. Teeth cleaner and smoother. | No bleeding. Stains removed noticeably. |
| P.S. | 39 | M | 4 | 1 | Routine | Teeth cleaner silky polished feeling. | Teeth brighter. |
| M.S. | 52 | M | 4 | 2 | Routine | Deodorized mouth. Persistent stains removed. | Persistent stains removed. Deodorized mouth. |
| S.T. | 48 | M | 4 | 1 | Routine | Calculus removed. Stain re- | Patient is a dentist. |

TABLE I-continued

| Name | Age | Sex | Prep. Used | No. of weeks used | Diagnosis (or reasons for use) | Voluntary Comment | Observation |
|------|-----|-----|------------|-------------------|--------------------------------|-------------------|-------------|
| | | | | | | moved. Polished teeth. | Calculus was removed. Teeth brighter. Stains removed. |
| J.P. | 21 | F | 4 | 1 | Routine | Whitened teeth. | Stains removed. Brightened teeth. |
| M.K. | 28 | M | 4 | 1 | Routine | Terrific polishing effect. Removed stains. | Patient is a dentist. Teeth brightened. |
| K.C. | 40 | F | 5 | 2 | Routine | Teeth felt cleaner and polished. Not satisfied to use any other tooth paste. | Stains removed. Teeth brighter. |
| U.V. | 42 | F | 5 | 1 | Routine | Liked taste-teeth felt cleaner. | Stains removed. Teeth brightened. |
| P.G. | 45 | F | 5 | 1 | Routine | Teeth felt cleaner. | Teeth brighter. |
| J.D. | 30 | F | 5 | 1 | Routine | Teeth felt clean in morning after night-time brushing. | Stains removed. Teeth brightened. |
| J.N. | 25 | F | 3 | 2 | Chronic Periodontitis | Reduced bleeding. Less sensitivity of gums. | Edema & bleeding diminished. |
| M.C. | 56 | F | 3 | 3 | Routine | Teeth felt very clean and smooth. | Teeth brighter and stains removed. |
| J.M. | 45 | F | 3 | 2 | Hypersensitivity | Hypersensitivity relieved. Teeth felt smooth. | Hypersensitivity relieved. Improvement in tooth paste |
| N.N. | 35 | M | 3 | 2 | Gingivitis & unusual stains. | Bleeding stopped. | Edema & bleeding markedly diminished. Stains removed. |
| B.M. | 50 | F | 3 | 2 | Periodontitis and hypersensitivity. | Soothing effect on gums. Teeth were no longer sensitive. | Gingival tone & color improved. Hypersensitivity relieved. |
| R.D. | 60 | F | 3 | 2 | Periodontitis | Teeth felt smooth. Gums no longer irritated. | Marked improvement in periodontal condition. Unusual rate of calculus deposition markedly retarded |
| C.H. | 34 | F | 3 | 2 | Periodontitis with heavy calculus deposition. | Teeth & gums were no longer sensitive or irritated. | Noticeable retardation of calculus formation. Edema and bleeding diminished Color and tone of gingiva improved. |
| J.P. | 40 | F | 6 | 2 | Periodontitis | Diminished bleeding. Smooth silky feeling of teeth. | Marked reduction in plaque accumulation. Edema reduced. |
| L.V. | 23 | F | 6 | 1 | Gingivitis | Soothing effect on gums. Bleeding stopped completely. | Gingiva returned to normal color and texture. Bleeding stopped. |
| R.F. | 58 | M | 6 | 3 | Hypersensitive dentin and periodontitis | Sensitivity relieved and bleeding diminished. | Improvement in color and gingival tone. No bleeding-no sensitivity to explorer |
| F.B. | 45 | F | 6 | 1 | Gingivitis and persistent stain. | Deodorizing effect-smooth feeling of teeth-no longer any bleeding. | Bleeding arrested-stains noticeably absent-deodorizing effect. |
| C.K. | 60 | F | 6 | 2 | Hypersensitive dentin, gingival recession. | Teeth no longer sensitive. | Hypersensitivity to air, cold and explorer relieved |
| B.P. | 35 | F | 6 | 2 | Periodontitis and hypersensitivity. | Pain in gums and teeth relieved. Mouth odor disappeared. | Gingival bleeding diminished, hypersensitivity relieved. Improvement in gingival tone and color. |
| Z.B. | 51 | F | 6 | 6 | Routine | Mouth felt very clean and smooth. This feeling persisted for many hours after tooth paste was used. | Patient's own dentist observed that she did not require her routine prophylaxis (given at 3 months interval) since using 22871. |

*NOTE THE PREDOMINANT COMMENTS BY PATIENTS OF "FRESHNESS CLEAN, SMOOTH & SILKY FEELING""POLISHED EFFECT" INDICATES THE REMOVAL OF PLAQUE OR PELLICLE.

The safety of the strontium EDTA dentifrice for use in contact with dental surfaces was determined by the Continuous Immersion Test, described at column 4, the first paragraph, of U.S. Pat. No. 3,584,116, issued June 8, 1971, as follows:

Mature human teeth, free of caries and obtained from patients requiring odontectomy (due to hopeless periodontal involvement) were immersed in aqueous solutions of the strontium EDTA dentifrice containing two grams of dentifrice in three milliters of water at physiologically tolerable pH ranges. Every four hours the teeth were examined for decalcification. Under visible light, enamel decalcification can be detected by a loss of luster with opaque spots or slight surface roughening. The teeth were examined microscopically and macroscopically at the end of seven days. No decalcification was observed through this period and hence the dentifrice caused no damage to dental enamel and is considered safe in this respect for use in the oral cavity.

The foregoing, specifically exemplified, various types of dentifrices need not be confined to their respective particular compositions recited in the illustrative examples. Alternatively, their respective individual ingredients, for example, other than the strontium disodium EDT can be varied individually in amounts used or can be omitted entirely or replaced by others ordinarily used for relatively similar purposes, so long as they are compatible with the strontium chelate or chelating agent present and contain no metallic cations that are chelated preferentially to strontium, and likewise are compatible with the other ingredients, as desired, within the skill of those occupied in this art.

The strontium chloride of the Examples can be replaced by some other strontium salt that is non-toxic and non-discoloring-to-the-teeth in the dosage and regimen used, for example, by another water-soluble strontium salt of an inorganic acid, such as another halide as its bromide, or its nitrate, or of an organic acid, as its formate, acetate, citrate, gentisate, gluconate, or salicylate.

Such strontium salt used in any of the examples need not be used alone for more than one of them may be used. In any case, it is advisable that the quantity of such strontium salt or salts used be sufficient to form, when in use, the strontium chelate with the total amount of free chelating agent present in the dentifrice.

The expression "pharmacologically innocuous" used herein is the recognized equivalent for the expression "therapeutically acceptable" often used to designate a substance which is physiologically and pharmacologically innocuous when taken in a dosage and in a regimen (i.e. frequency of administration) that is effective for its indicated therapeutically useful application, and thus is pharmacologically harmless.

We claim:

1. The method of improving oral hygiene by applying to the teeth a water-containing dentifrice comprising a substantially stable solution of a non-toxic, water-soluble ionic strontium chelate of ethylene diamine tetracetic acid selected from (a) strontium disodium ethylene diamine tetracetate and (b) the reaction product in aqueous medium of a water-soluble salt of ethylene diamine tetracetic acid and a molar equivalent amount of a pharmacologically innocuous water-soluble strontium salt that can react in an aqueous medium with such ethylene diamine tetracetic acid salt to give the corresponding strontium ethylene diamine tetracetate chelate, the strontium ethylene diamine tetracetate chelate constituting an amount sufficient to provide improvement in treatment of gingivitis and periodonitis up to about 10%, measured as the strontium cation of said chelate, by weight of said dentifrice, and said dentifrice being characterized by the substantial absence of substances which precipitate said strontium.

2. The method of claim 1 in which the strontium cation constitutes from about 2.5% to about 10% by weight of said dentifrice.

3. The method of claim 1 in which the strontium cation constitutes from about 2.5% to about 7.5% by weight of said dentifrice.

4. The method of claim 1 in which said dentifrice is a toothpaste.

* * * * *